United States Patent
Bechwati et al.

(10) Patent No.: US 11,717,252 B2
(45) Date of Patent: Aug. 8, 2023

(54) AI-BASED RENDERED VOLUME AUTO-CORRECTION FOR FIXED AND MOBILE X-RAY IMAGING MODALITIES AND OTHER IMAGING MODALITIES

(71) Applicant: NeuroLogica Corporation, a subsidiary of Samsung Electronics Co., Ltd., Danvers, MA (US)

(72) Inventors: Ibrahim Bechwati, Waltham, MA (US); Philip Sullivan, Danvers, MA (US)

(73) Assignee: NeuroLogica Corporation, a subsidiary of Samsung Electronics Co., Ltd., Danvers, MA (US)

( * ) Notice: Subject to any disclaimer, the term of this patent is extended or adjusted under 35 U.S.C. 154(b) by 890 days.

(21) Appl. No.: 16/531,503

(22) Filed: Aug. 5, 2019

(65) Prior Publication Data
US 2020/0037981 A1    Feb. 6, 2020

Related U.S. Application Data

(60) Provisional application No. 62/714,396, filed on Aug. 3, 2018.

(51) Int. Cl.
*A61B 6/00* (2006.01)
*A61B 6/03* (2006.01)
(Continued)

(52) U.S. Cl.
CPC .............. *A61B 6/586* (2013.01); *A61B 6/032* (2013.01); *A61B 6/4405* (2013.01); *A61B 6/542* (2013.01);
(Continued)

(58) Field of Classification Search
CPC ....... A61B 6/586; A61B 6/032; A61B 6/4405; A61B 6/542; A61B 6/584; A61B 6/0492;
(Continued)

(56) References Cited

U.S. PATENT DOCUMENTS

| | | | |
|---|---|---|---|
| 4,352,020 | A | 9/1982 | Horiba et al. |
| 4,962,514 | A | 10/1990 | Hart et al. |

(Continued)

OTHER PUBLICATIONS

Mennessier C. et al., Distortion Correction, Geometric Calibration, and Volume Reconstruction for an Isocentric C-Arm X-Ray System, IEEE Nuclear Science Symposium Conference Record, Oct. 2011, pp. 2943-2947.

*Primary Examiner* — Peter Luong
(74) *Attorney, Agent, or Firm* — Pandiscio & Pandiscio

(57) ABSTRACT

A method for correcting inaccuracies in a three-dimensional (3D) rendered volume of an object due to deviations between an actual scanner translation speed and an expected scanner translation speed, the method comprising: placing a pre-measured reference adjacent to the object which is being scanned so that the pre-measured reference and the object are in the same scan field; scanning the object and the pre-measured reference so that the object and the pre-measured reference are both incorporated in a 3D rendered volume produced through scanning; comparing the 3D rendered volume of the pre-measured reference against the 3D volume of the true pre-measured reference and generating a correction map indicative of how the rendered 3D volume of the pre-measured reference should be adjusted so as to produce a more accurate 3D rendering of the pre-measured reference; and using the correction map to adjust the rendered 3D volume of the object.

25 Claims, 11 Drawing Sheets

The true and the reconstructed rulers in the case of ideal speed.

(51) Int. Cl.
  *A61B 90/00* (2016.01)
  *G16H 30/40* (2018.01)

(52) U.S. Cl.
  CPC .............. *A61B 6/584* (2013.01); *A61B 90/39* (2016.02); *G16H 30/40* (2018.01); *A61B 2090/3966* (2016.02)

(58) Field of Classification Search
  CPC ............ A61B 90/39; A61B 2090/3966; A61B 2017/0092; G16H 30/40; G16H 40/63; G06T 2211/412; G06T 11/008
  See application file for complete search history.

(56) References Cited

U.S. PATENT DOCUMENTS

| | | | |
|---|---|---|---|
| 5,301,108 A | 4/1994 | Hsieh | |
| 5,615,279 A | 3/1997 | Yoshioka et al. | |
| 5,651,046 A | 7/1997 | Floyd et al. | |
| 5,774,519 A | 6/1998 | Lindstrom et al. | |
| 5,867,553 A | 2/1999 | Gordon et al. | |
| 6,040,580 A | 3/2000 | Watson et al. | |
| 6,148,057 A | 11/2000 | Urchuck et al. | |
| 6,178,220 B1 | 1/2001 | Freundlich et al. | |
| 6,400,789 B1 | 6/2002 | Dafni | |
| 6,408,044 B2 | 6/2002 | Sembritzki et al. | |
| 6,568,851 B2 | 5/2003 | Saito | |
| 6,597,803 B1 | 7/2003 | Pan et al. | |
| 6,683,934 B1 | 1/2004 | Zhao et al. | |
| 6,813,374 B1 | 11/2004 | Karimi et al. | |
| 6,848,827 B2 | 2/2005 | Wu et al. | |
| 6,944,258 B2 | 9/2005 | Nukui et al. | |
| 7,086,780 B2 | 8/2006 | Wu et al. | |
| 7,088,800 B2 | 8/2006 | Nukui et al. | |
| 7,108,424 B2 | 9/2006 | Heumann et al. | |
| 7,134,787 B2 | 11/2006 | Sun et al. | |
| 7,175,347 B2 | 2/2007 | Tybinkowski et al. | |
| 7,428,290 B2 | 9/2008 | Nishide et al. | |
| 7,555,097 B2 | 6/2009 | Yamazaki | |
| 7,724,866 B2 | 5/2010 | Naidu | |
| 8,121,250 B2 | 2/2012 | Dafni et al. | |
| 8,315,352 B2 | 11/2012 | Wu et al. | |
| 8,358,824 B2 | 1/2013 | Hagiwara | |
| 8,503,750 B2 | 8/2013 | Benson et al. | |
| 8,611,625 B2 | 12/2013 | Oohara | |
| 8,611,627 B2 | 12/2013 | Wu et al. | |
| 8,686,368 B2 | 4/2014 | Tybinkowski et al. | |
| 8,818,058 B2 | 8/2014 | Paul et al. | |
| 8,888,364 B2 | 11/2014 | Bailey et al. | |
| 9,208,918 B2 | 12/2015 | Tybinkowski et al. | |
| 9,285,326 B2 | 3/2016 | Gagnon et al. | |
| 9,683,948 B2 | 6/2017 | Gao et al. | |
| 9,852,526 B2 | 12/2017 | Nakanishi | |
| 2003/0058994 A1 | 3/2003 | Sembritzki | |
| 2004/0196960 A1 | 10/2004 | Tanigawa et al. | |
| 2004/0228451 A1 | 11/2004 | Wu et al. | |
| 2005/0013414 A1 | 1/2005 | Sun et al. | |
| 2006/0159223 A1 | 7/2006 | Wu et al. | |
| 2010/0027867 A1 | 2/2010 | Bernhardt et al. | |
| 2010/0195804 A1 | 8/2010 | Dafni et al. | |
| 2011/0293161 A1 | 12/2011 | Yi et al. | |
| 2012/0163557 A1 | 6/2012 | Hsieh et al. | |
| 2013/0026353 A1 | 1/2013 | Yan et al. | |
| 2013/0156163 A1 | 6/2013 | Liu et al. | |
| 2014/0072108 A1 | 3/2014 | Rohler et al. | |
| 2014/0321608 A1 | 10/2014 | Ueki et al. | |
| 2016/0030133 A1* | 2/2016 | Ramsey | A61B 6/583 378/163 |
| 2016/0074002 A1 | 3/2016 | Bechwati et al. | |
| 2016/0157809 A1 | 6/2016 | Takahashi et al. | |
| 2016/0203241 A1 | 7/2016 | Dean et al. | |
| 2017/0140560 A1 | 5/2017 | Kraus et al. | |
| 2017/0281117 A1 | 10/2017 | Sullivan et al. | |
| 2018/0095450 A1 | 4/2018 | Lappas et al. | |

* cited by examiner

*The true and the reconstructed rulers in the case of ideal speed.*

The true and the reconstructed ruler with 2.5% slower scanner.

The true and reconstructed ruler for a 2.5% faster scanner.

TREE-BASED DECISIONS USING THE 3 BEST CHOICES

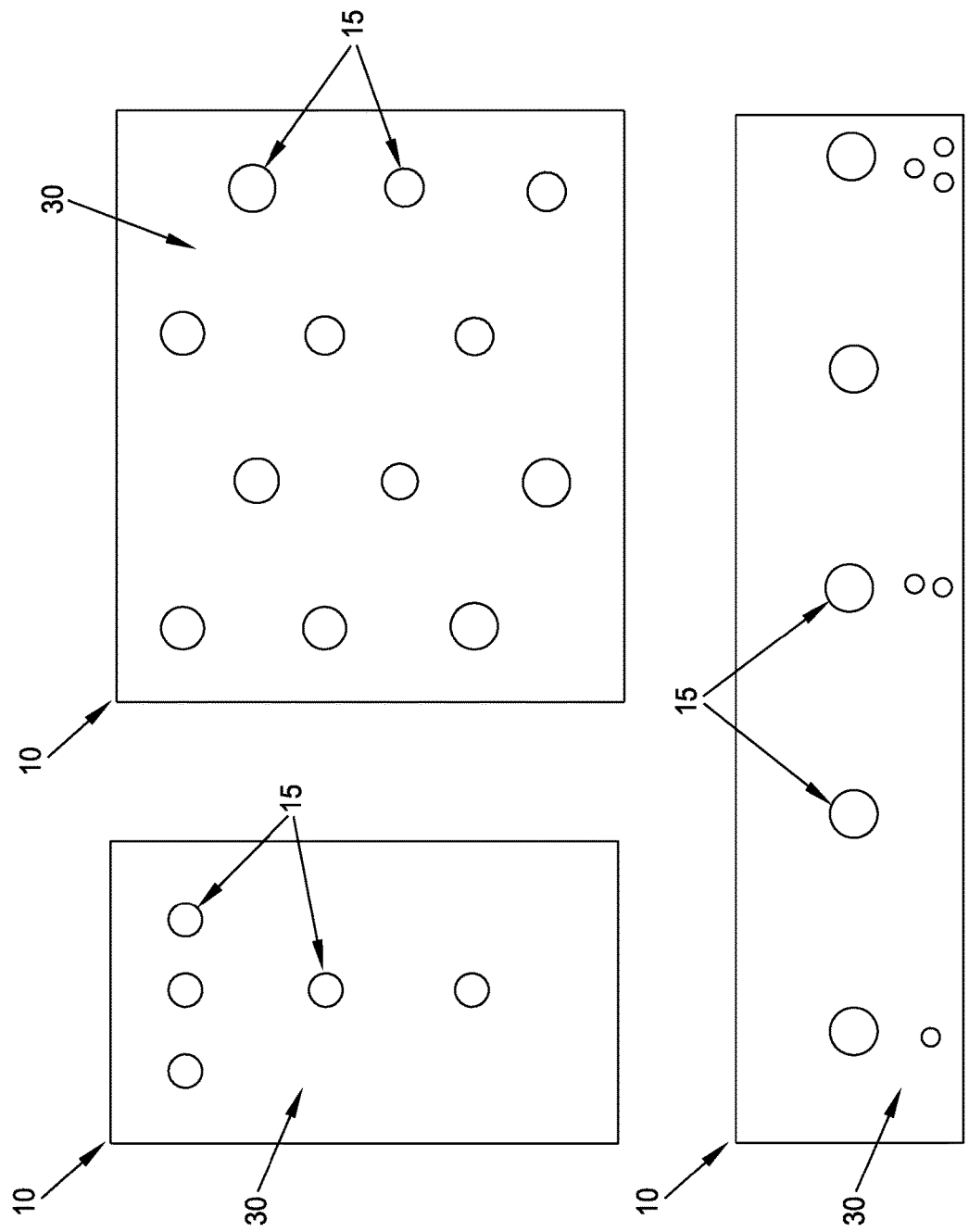

AI-BASED RENDERED VOLUME AUTO-CORRECTION FOR FIXED AND MOBILE X-RAY IMAGING MODALITIES AND OTHER IMAGING MODALITIES

REFERENCE TO PENDING PRIOR PATENT APPLICATION

This patent application claims benefit of pending prior U.S. Provisional Patent Application Ser. No. 62/714,396, filed Aug. 3, 2018 by NeuroLogica Corporation and Ibrahim Bechwati et al. for Al-BASED RENDERED VOLUME AUTO-CORRECTION FOR FIXED AND MOBILE X-RAY IMAGING MODALITIES AND OTHER IMAGING MODALITIES, which patent application is hereby incorporated herein by reference.

FIELD OF THE INVENTION

This invention relates to imaging in general, and more particularly to the correction of rendered volumes produced during imaging.

BACKGROUND OF THE INVENTION

Introduction

Artificial Intelligence (AI) is the ability of a machine to learn and react to changes in its working environment. The academic concept of artificial intelligence is very old: it goes back at least as far as 1956. However, machines that sense the surrounding environment and react to that surrounding environment existed much earlier. For example, the simple thermostat, which was invented in the late 1800's, controls the heating and cooling of a room, and can easily be classified as an intelligent machine. The thermostat senses the temperature in the room and makes a decision, without human intervention, to turn on or turn off the heating or cooling apparatus. However, the classification of a machine as an AI machine is typically based more on its complexity than its purpose. For instance, Optical Character Recognition (OCR) and Continuous Speech Recognition (CSR) topped the list of AI projects back in the 1980's, but they are now often dropped from lists of AI projects in favor of more complex applications such as Autonomous Vehicles, etc.

The components of a successful AI application are generally: 1) a mechanism to provide measurements (typically analog or digital data provided by sensors); 2) mathematical algorithms that analyze the input data and make a decision; and 3) a learning or training mechanism that "teaches" the machine how to behave under different environmental conditions with, optionally, a mechanism to self-test and validate.

The Problem

The performance of any imaging modality depends on the accuracy and the truthfulness (i.e., fidelity) of the three-dimensional (3D) volume created (i.e., rendered) through imaging. In addition, the accuracy of a surgical navigation system, and the success of auto-registration in a surgical navigation system, depends on the accuracy and truthfulness (i.e., fidelity) of the 3D volume created (i.e., rendered) through imaging.

The accuracy and truthfulness (i.e., fidelity) of a 3D volume created (i.e., rendered) through imaging depends on the translation accuracy of the imaging modality. For example, with CT imaging, the CT machine may be fixed and the patient support may be moving ("fixed CT imaging"), such as is shown in FIG. 1; or the patient support may be fixed and the CT machine may be moving ("mobile CT imaging"), such as is shown in FIG. 2. In either case, one element is moving relative to another element during scanning. Similar arrangements occur in other imaging modalities. With these imaging modalities, the translational accuracy of the system (i.e., the accuracy with which one element moves relative to another element during scanning) is generally reflected in the accuracy and truthfulness (i.e., fidelity) of the 3D volume created (i.e., rendered) through imaging: the greater the translational accuracy of the system (be it the movement of the patient support relative to the scanner or the movement of the scanner relative to the patient support), the greater the accuracy and truthfulness (i.e., fidelity) of the rendered 3D volume. And where the rendered 3D volume is used in a surgical navigation system, the greater the translational accuracy of the scanner, the greater the accuracy of the surgical navigation system, and the greater the success of auto-registration in the surgical navigation system.

Thus, it is desirable to provide a new and improved method and apparatus for increasing the rendering accuracy of scanning systems.

SUMMARY OF THE INVENTION

The present invention comprises a new and improved method and apparatus for increasing the rendering accuracy of an imaging modality.

More particularly, the method of the present invention comprises placing a pre-measured reference (i.e., a reference having markings set with pre-determined spacings) adjacent to the object which is being scanned so that the pre-measured reference is incorporated in the 3D volume created (i.e., rendered) through imaging. The imaged reference (i.e., the 3D rendered volume of the pre-measured reference) is then compared to the true pre-measured reference. This comparison between the rendered 3D volume of the pre-measured reference and the true pre-measured reference is used to create a "correction map" that can be used to create a more truthful (i.e., more accurate) 3D rendering of the scanned volume. The imaged (i.e., rendered) 3D volume is then adjusted, based on the results of the comparison (i.e., using the "correction map") so as to provide a more accurate 3D rendering of the scanned volume.

Note that this reference-based auto-correction scheme may be applied to an imaging modality which comprises a moving CT machine and a fixed patient support ("fixed CT imaging"), or it may be applied to an imaging modality which comprises a fixed CT machine and a moving patient support ("mobile CT imaging"). This reference-based auto-correction scheme may also be applied to other imaging modalities. Note also that where the imaging modality comprises a moving CT machine and a fixed patient support, the moving CT machine may be a free-moving mobile scanner (e.g., a mobile scanner supported on wheels or centipede belts), or the moving CT machine may be a guided mobile scanner (e.g., a mobile scanner supported on rails or tracks).

In addition to creating a "correction map" for increasing the accuracy of the rendered 3D volume, the pre-measured reference can also be used to automatically calibrate the translation speed of the moving portion of the imaging modality (e.g., the moving patient support or the moving CT machine), and to make a decision as to whether a correction to the translation speed is needed or not. In other words, where the imaging modality comprises a fixed CT machine and a moving patient support, the pre-measured reference can be used to calibrate the translation speed of the moving patient support and adjust that translation speed if necessary; or where the imaging modality comprises a moving CT machine and a fixed patient support, the pre-measured reference can be used to calibrate the translation speed of the moving CT machine and adjust that translation speed if necessary. Again, this is done by determining the difference between the imaged (i.e., rendered) 3D volume of the pre-measured reference incorporated in the rendered 3D volume and the actual pre-measured reference.

The pre-measured reference can be embedded in, or attached to, or laid on, etc. the patient support (which can be a table, a head holder, etc.) or located anywhere in the scanner, so long as the pre-measured reference can be imaged with the volume which is being scanned. By way of example but not limitation, the patient support may comprise a scan table covered by a cushion (upon which the patient rests), and the pre-measured reference may be mounted to the scan table below the cushion.

This new method includes all of the elements needed to provide an intelligent imaging modality that measures, and corrects for, any inaccuracies in the rendered 3D volume which are due to translation speed inaccuracies resulting from the environment in which the scan is taken (e.g., floor inaccuracies, drive system inaccuracies, bumps on a vehicle floor, etc.). The pre-measured reference and the scanner itself are the measuring instruments which provide the needed input to the method (i.e., they provide the reference object and the rendered 3D volume which includes the rendered reference object). The method also includes related mathematical algorithms which are used to auto-extract information from the rendered 3D volume (i.e., to auto-extract the rendered 3D volume of the pre-measured reference and to auto-extract the rendered 3D volume of the scanned object, e.g., patient anatomy). The present invention is capable of taking this information and finding a match, from within the millions of possible hypotheses, to identify the rendered 3D volume of the pre-measured reference within the complete rendered 3D volume (i.e., the rendered 3D volume of the object which is being scanned and the pre-measured reference which is being scanned). Then, after comparing the rendered 3D volume of the pre-measured reference against the true pre-measured reference and determining the aforementioned "correction map", the present invention can make the necessary correction to the rendered 3D volume if it is deemed necessary to counteract (i.e., correct for) inaccuracies introduced into the rendered 3D volume during imaging (i.e., due to translational inaccuracies in the moving elements of the imaging system). In accordance with the invention, the imaging modality is "taught" to make a decision whether a correction is beneficial, needed or not required.

In one preferred form of the invention, there is provided a method for correcting inaccuracies in a three-dimensional (3D) rendered volume of an object due to deviations between an actual scanner translation speed and an expected scanner translation speed, the method comprising:

placing a pre-measured reference adjacent to the object which is being scanned so that the pre-measured reference and the object are in the same scan field;

scanning the object and the pre-measured reference so that the object and the pre-measured reference are both incorporated in a 3D rendered volume produced through scanning;

comparing the 3D rendered volume of the pre-measured reference against the 3D volume of the true pre-measured reference and generating a correction map indicative of how the rendered 3D volume of the pre-measured reference should be adjusted so as to produce a more accurate 3D rendering of the pre-measured reference; and using the correction map to adjust the rendered 3D volume of the object.

In another preferred form of the invention, there is provided a method for correcting inaccuracies in a three-dimensional (3D) rendered volume of an object due to deviations between an actual scanner translation speed and an expected scanner translation speed, the method comprising:

creating a 3D rendered volume of the object and a pre-measured reference;

extracting information regarding the 3D rendered volume of the pre-measured reference from the 3D rendered volume of the object and the pre-measured reference;

comparing the extracted information regarding the 3D rendered volume of the pre-measured reference to the corresponding information of the actual pre-measured reference;

determining the extent of the deviation of the 3D rendered volume of the pre-measured reference from the information of the actual pre-measured reference;

correcting the 3D rendered volume of the object based on the foregoing determination of the extent of the deviation of the 3D rendered volume of the pre-measured reference from the information of the actual pre-measured reference;

extracting information regarding the 3D rendered volume of the pre-measured reference from the corrected 3D rendered volume of the object and the pre-measured reference; and comparing the extracted information regarding the 3D rendered volume of the pre-measured reference to the corresponding information of the actual pre-measured reference.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 10 is a schematic view showing other forms of pre-measured references.

DETAILED DESCRIPTION OF THE PREFERRED EMBODIMENTS

Background

The present invention addresses the rendering accuracy of imaging systems, e.g., CT scanners.

As mentioned above, there are two types of imaging modalities: the class of fixed scanners (i.e., the fixed imaging modality) and the class of mobile scanners (i.e., the mobile imaging modality).

The translational accuracy of the fixed scanner is driven by the translational accuracy of moving the patient support (e.g., the table or bed). With a fixed imaging modality, the fixed scanner gantry is stationary ("fixed") and the patient is moved in and out of the scan zone ("plan") using a mounted scanning table or bed. The patient table or bed is, by design, well-leveled and moves on a well-defined trajectory driven by high precision rails. They have an accuracy of 0.25 mm. This will serve as the "gold standard" of translational accuracy.

The translational accuracy of the mobile scanner is driven by the translational accuracy of the moving scanner.

Mobile scanners can be divided into two sub-classes. The first sub-class includes scanners that move on a platform guided by rails. The second sub-class includes free-moving scanners that move over the floor using wheels or centipedes.

In imaging mode, scanners of the first sub-class do not move on the floor: instead, they move on a well-leveled platform which helps overcome any variation in the floor. The rails ensure that the scanner will travel in a straight line. With scanners of the first sub-class, the scan platforms have good translational accuracy but they reduce the scanner mobility and require more space.

Scanners of the second sub-class are truly mobile scanners: they do not use any platform or rails. Instead, they are free to move on any floor of any structure (e.g., room, vehicle, etc.) that is large enough to accommodate them. However, with scanners of the second sub-class, the translational accuracy of the scanners is affected by the floor they are moving on. Any variation in the floor (such as bumps, ramps or inclines) affects the translational accuracy of the scanner (and hence affects the accuracy of the rendered 3D volume produced by the scanner). Thus, with scanners of this second sub-class, the translational accuracy of the scanner is highly dependent on the floor where the scan is being conducted.

With fixed CT imaging, a variation in the speed of movement of the patient support (i.e., the patient support moving faster or slower than its intended speed) causes positioning errors in the rendered 3D volume; and with mobile CT imaging, a variation in the speed of movement of the scanner (i.e., the scanner moving faster or slower than its intended speed) causes positioning errors in the rendered 3D volume.

By way of example but not limitation, consider the case of a moving scanner, where the scanner moves at (i) the ideal speed (i.e., the expected speed), (ii) a slower speed (i.e., slower than the expected speed) and (iii) a faster speed (i.e., faster than the expected speed).

Figure 1:
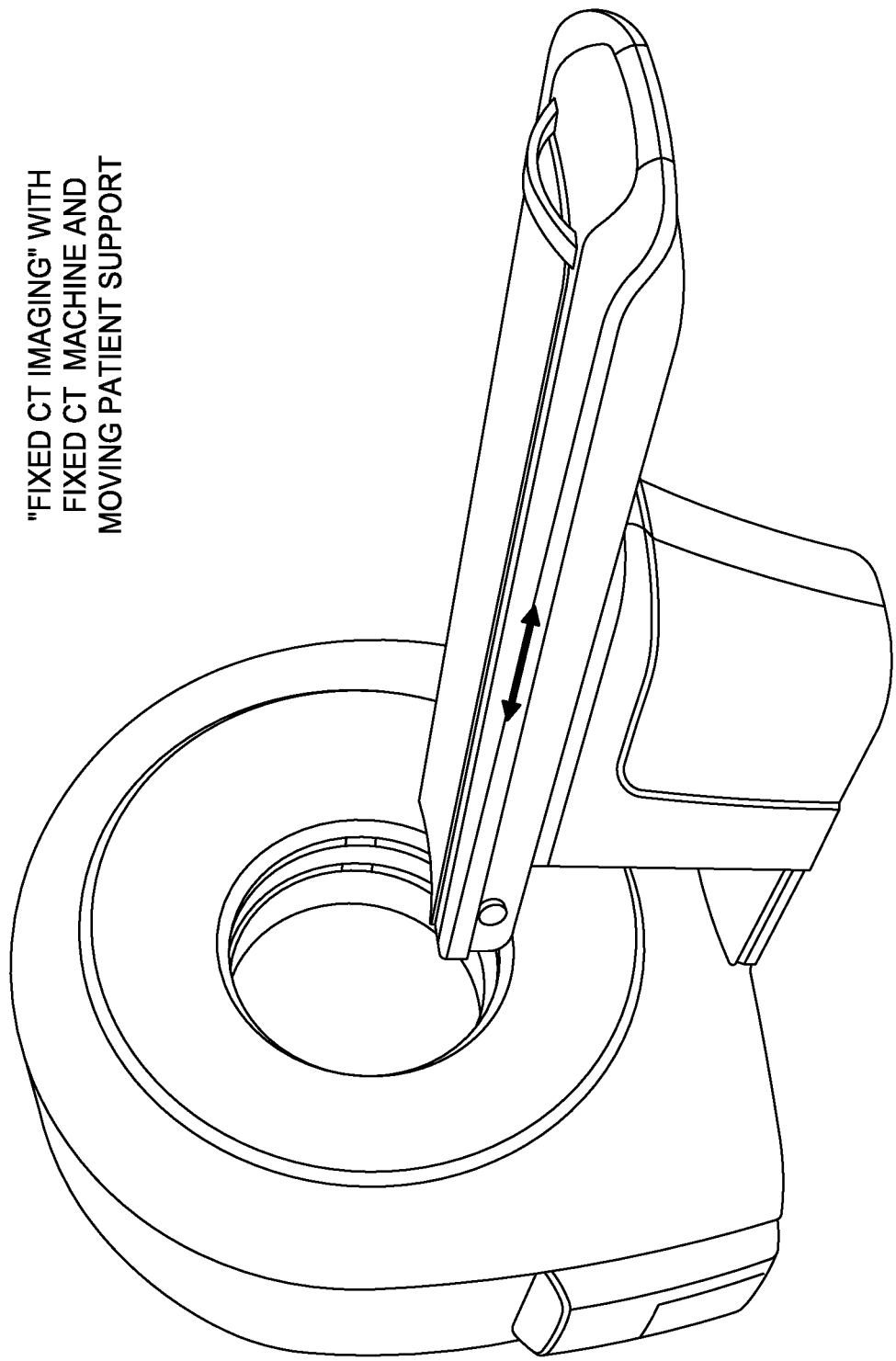
FIG. 1 is a schematic view showing fixed CT imaging where the CT machine may be fixed and the patient support may be moving.
Figure 2:
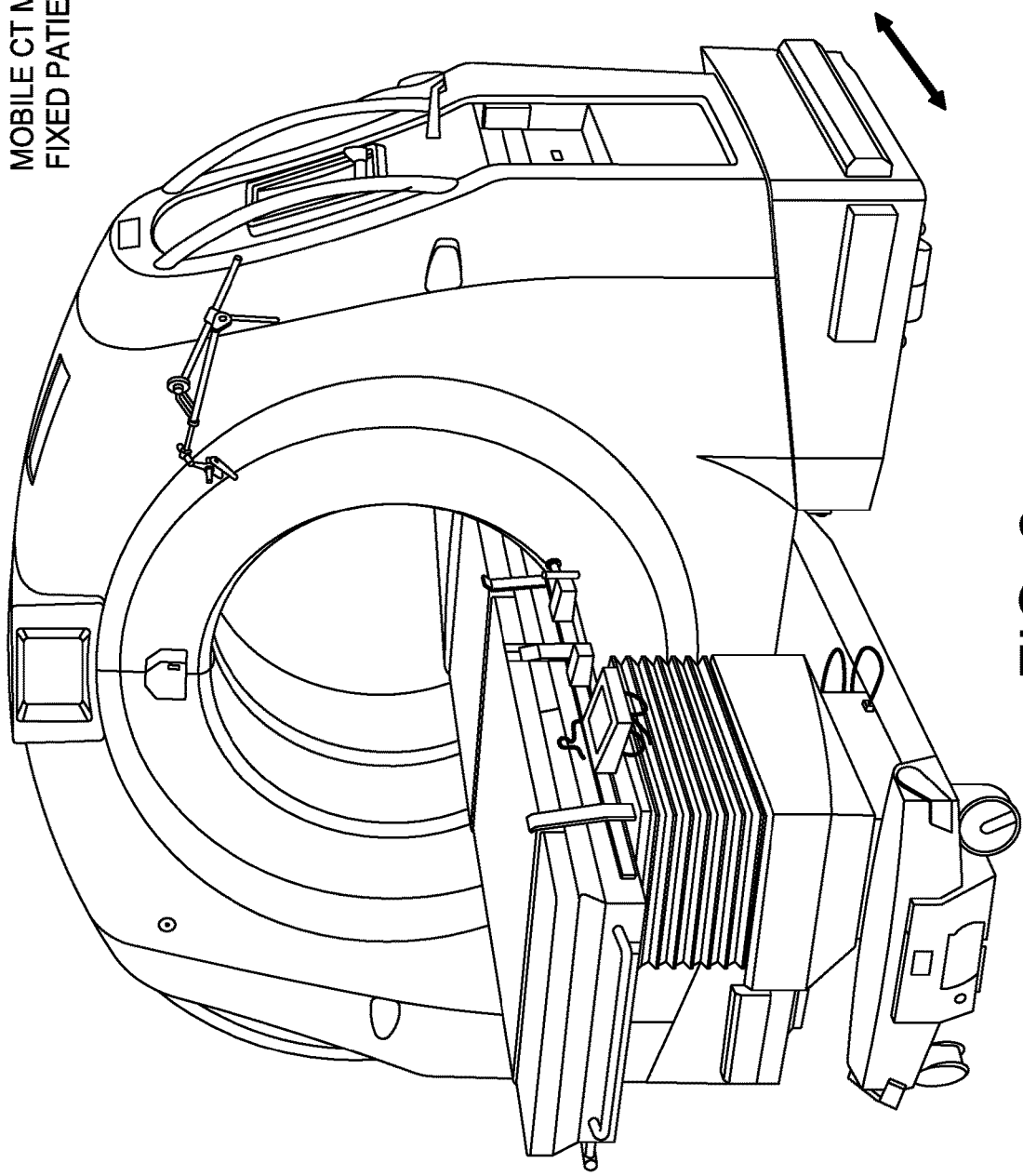
FIG. 2 is a schematic view showing mobile CT imaging, where the patient support may be fixed and the CT machine may be moving.
Figure 3:
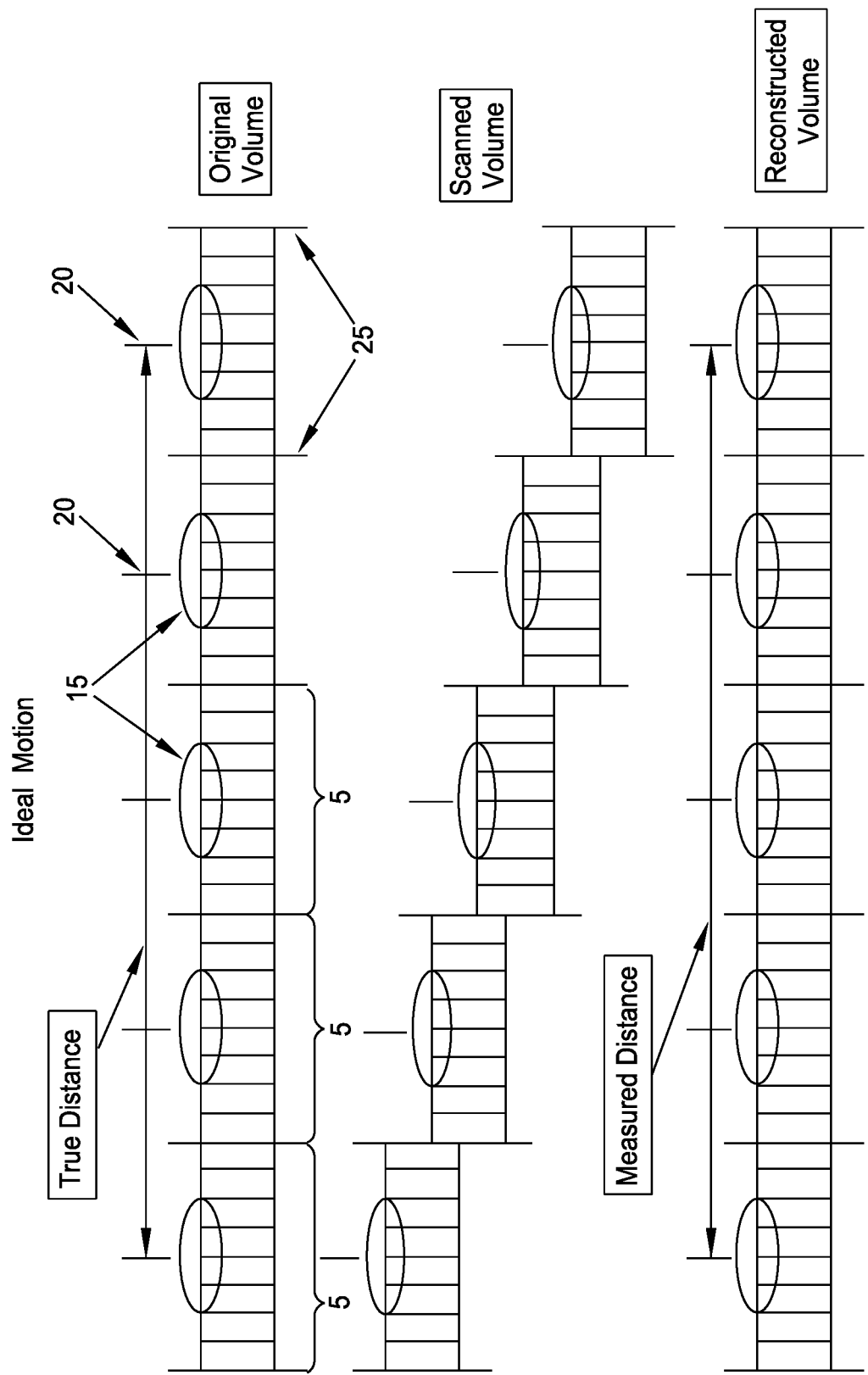
FIG. 3 is a schematic view showing the scanned sections of a scanned pre-measured reference (e.g., a ruler with beads) acquired with a moving scanner, wherein the scanner is moving at its intended speed.

Ideal Speed: Looking first at FIG. 3, in a normal scanning mode, the multi-row detectors (e.g., 8 rows of detectors in a so-called "8 slice CT machine") are capturing sections 5 of the scanned object, in this case a ruler 10 (FIG. 9) with uniformly-spaced beads 15. Note that ruler 10 with its uniformly-spaced beads 15 constitutes the pre-measured object referred to above. The top image in FIG. 3 shows the "true" ruler with scanner locations 20 and the scanned section markings 25 marked on the ruler. The middle image in FIG. 3 offsets each scan section 5 from its adjacent scan sections 5 for more clarity. The scan sections 5 are perfectly adjacent. The lower image in FIG. 3 represents the reconstructed volume built by joining the scanned sections from the middle image of FIG. 3. It is clear from FIG. 3 that where the actual scanner speed is the same as the intended scanner speed, the original volume and the reconstructed volume are identical.

Figure 4:
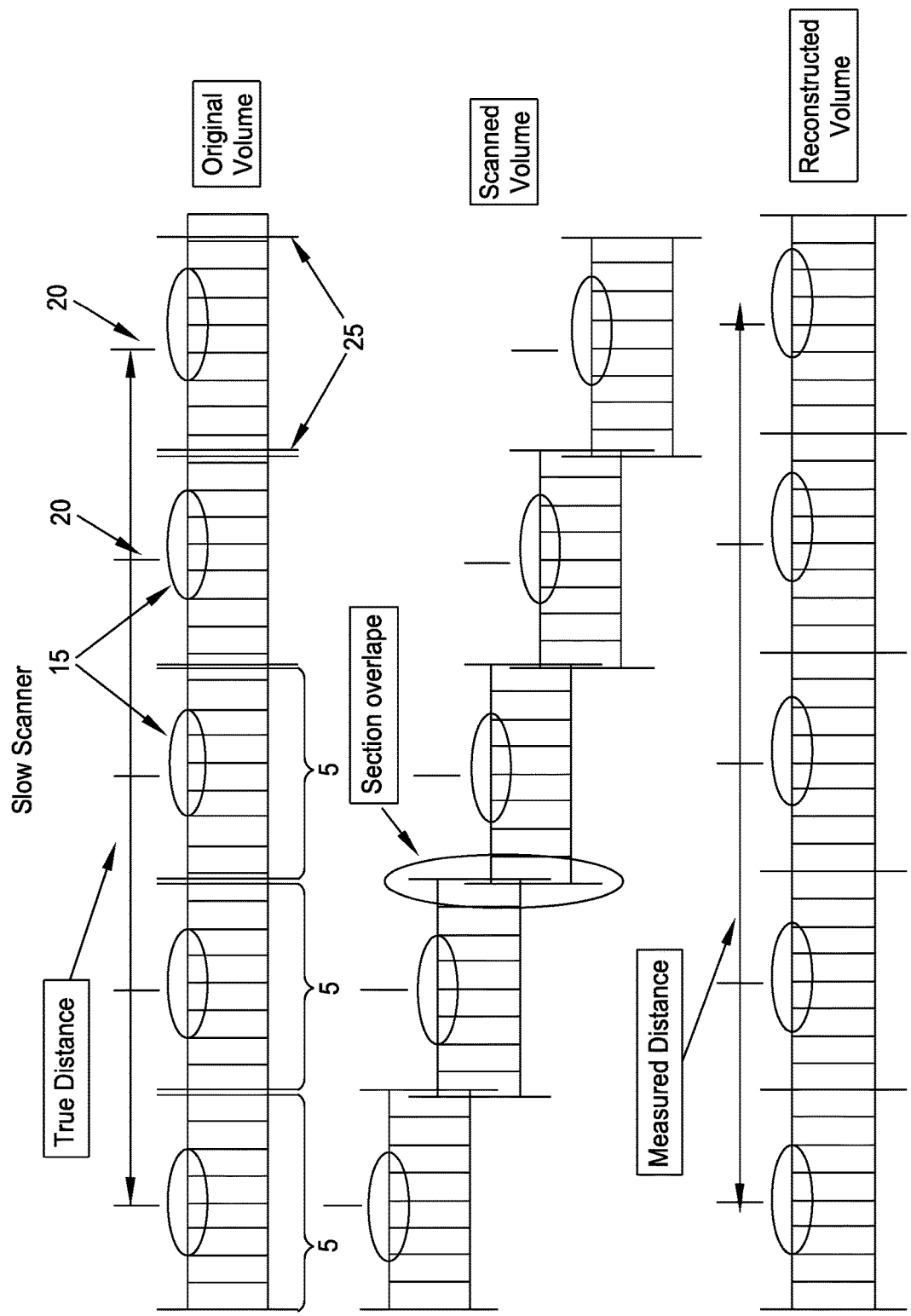
FIG. 4 is a schematic view showing the scanned sections of a scanned pre-measured reference (e.g., a ruler with beads) acquired with a moving scanner, wherein the scanner is moving slower than its intended speed.

Slow Speed: Looking next at FIG. 4, in the case of a "slow scanner" (i.e., a scanner running more slowly than its intended speed), the scanned sections 5 will slightly overlap according to difference between the expected scanner speed and the actual scanner speed. FIG. 4 shows the scan slices resulting from the scanner operating at a slower-than-expected speed. In this image, the actual speed of the scanner is 97.5% of the normal (i.e., expected) speed. The overlapping of the scanned sections 5 is clearly shown in the top and middle images of FIG. 4. The top image of FIG. 4 shows that the scanner will fall short of covering the true ruler. The top image of FIG. 4 also shows the location 20 of each of the scans. The locations 20 are shifted slightly to the left due to the slower-than-expected scanner speed (ideally, when the scanner is operating at the expected scanner speed, the scan locations are centered on the center of the bead 15 in each section, as seen in FIG. 3—but in the case of a "slow scanner", the scan locations 20 start to move off-center from the beads as the scan progresses, as seen in FIG. 4). The middle image of FIG. 4 shows more clearly how the scanned sections 5 overlap as a result of the slower-than-expected scanner speed. The bottom image of FIG. 4 shows the reconstructed volume of the ruler. Note that the reconstructed ruler shows a stretched volume. The measured distance is larger than the true distance. Thus, as a consequence of a slower-than-expected scanner, the reconstructed rendered object (i.e., the "reconstructed volume") appeared to be a stretched version of the original object (i.e., the "original volume").

Figure 5:
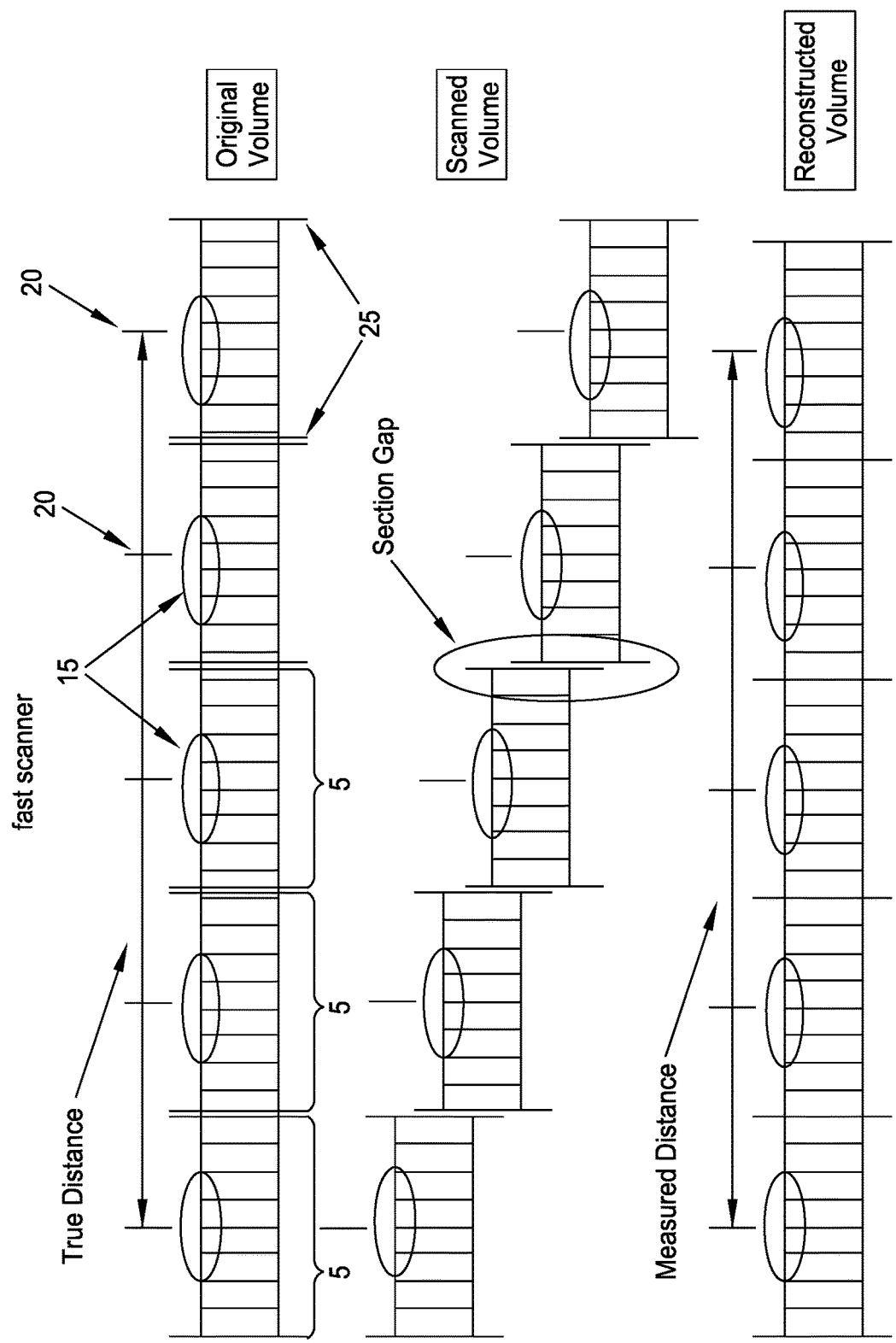
FIG. 5 is a schematic view showing the scanned sections of a scanned pre-measured reference (e.g., a ruler with beads) acquired with a moving scanner, wherein the scanner is moving faster than its intended speed.

Fast Speed: Looking next at FIG. 5, in the case of a "fast scanner" (i.e., a scanner running more quickly than its intended speed), there will be a slight gap between the scanned sections 5. FIG. 5 shows the scan slices resulting from the scanner operating at a faster-than-expected speed, and compares the "true" volume of the ruler with the reconstructed volume of the ruler in the case of a slight increase in the speed of the scanner (i.e., a scanner operating at faster-than-expected speed). The top image of FIG. 5 shows that a slight gap will exist between the scanned sections when the scanner is operating at a faster-thanexpected speed. FIG. 5 also shows the location of each section shifted to the right due to the faster-than-expected scanner speed (ideally, when the scanner is operating at the expected scanner speed, the scan locations are centered on the center of the bead 15 in each section, as seen in FIG. 3—but in the case of a "fast scanner", the scan locations start to move off-center from the beads as the scan progresses, as seen in FIG. 5). The middle image of FIG. 5 shows more clearly how the gaps between the scanned sections result from the faster-than-expected scanner speed. These gaps between the scanned sections 5 are shown in FIG. 5 as being the same size/length, however, the gaps between the scanned sections 5 could differ if the speed of the scanner varies during scanning, and in any case the error (i.e., the shift in the scan sections due to the difference between the actual scanner speed and the expected scanner speed) is the cumulative (i.e., summed) values of all the gaps, e.g., after 5 scans the error is the sum of the four gaps between the scanned sections. In this case the reconstructed rendered ruler (i.e., the "reconstructed volume") looks like a shrunken (i.e., shortened) version of the original ruler (i.e., the "original volume").

Thus, a variation in the speed of the scanner (i.e., the scanner moving faster or slower than its intended speed) causes positioning errors (i.e., misalignment of the scanned sections) in the rendered 3D volume.

In the past, two software-based approaches have been developed to help improve the translational accuracy of mobile CT scanners.

The first software-based approach is based on tracking the distance traveled by the scanner in axial mode (i.e., along the longitudinal axis of the scan), where the scanner translates in between scan sections to cover the entire scan volume. The distance traveled by the scanner is examined after each move, and a correction is introduced in the next move to compensate for any difference between the actual travel distance and the predicted (i.e., expected) travel distance. With this first software-based approach, the solution to the problem of translational accuracy (or, more precisely, translational inaccuracy) depends on feedback from the scanner (i.e., data relating to the distance actually traveled by the scanner).

The second software-based approach is to use a tilt sensor on the scanner to measure scanner tilt (and hence measure floor variation) and then use this information to improve translational accuracy. But this second approach is dependent on the location of the sensor on the scanner (i.e., the higher the tilt sensor is on the scanner, the more accurate the tilt data, and hence the more accurate the measure of floor variation). And in any case, with this second software-based approach, the solution to the problem of translational accuracy (or, more precisely, translational inaccuracy), depends on feedback from the scanner.

In yet another approach, where the scanner operates in a continuous translational mode, a speed calibration is introduced to improve the translational accuracy of the scanner.

The New Method

The new method of the present invention is an image-based correction. This implies that once the 3D volume is imaged, the imaging modality is no longer needed for the correction, i.e., everything required for correcting inaccuracies in the rendered 3D volume is already present in the rendered 3D volume (unlike the aforementioned first software-based approach and second software-based approach, which require feedback from the scanner). This is achieved by placing a pre-measured reference (e.g., a ruler 10 with its beads 15, see below) into the scan field so that the pre-measured reference is incorporated into the rendered 3D volume produced by the scan. The rendered 3D volume of the pre-measured reference may then be extracted from the complete rendered 3D volume (i.e., the rendered 3D volume of the patient anatomy being scanned and the pre-measured reference positioned in the scan field), and compared with the actual pre-measured reference, so as to generate a correction map which can be used to adjust the complete rendered 3D volume so as to correct for translational errors introduced by the scanner (i.e., by differences between the actual speed of the scanner vis-a-vis the expected speed of the scanner).

Figure 5A:
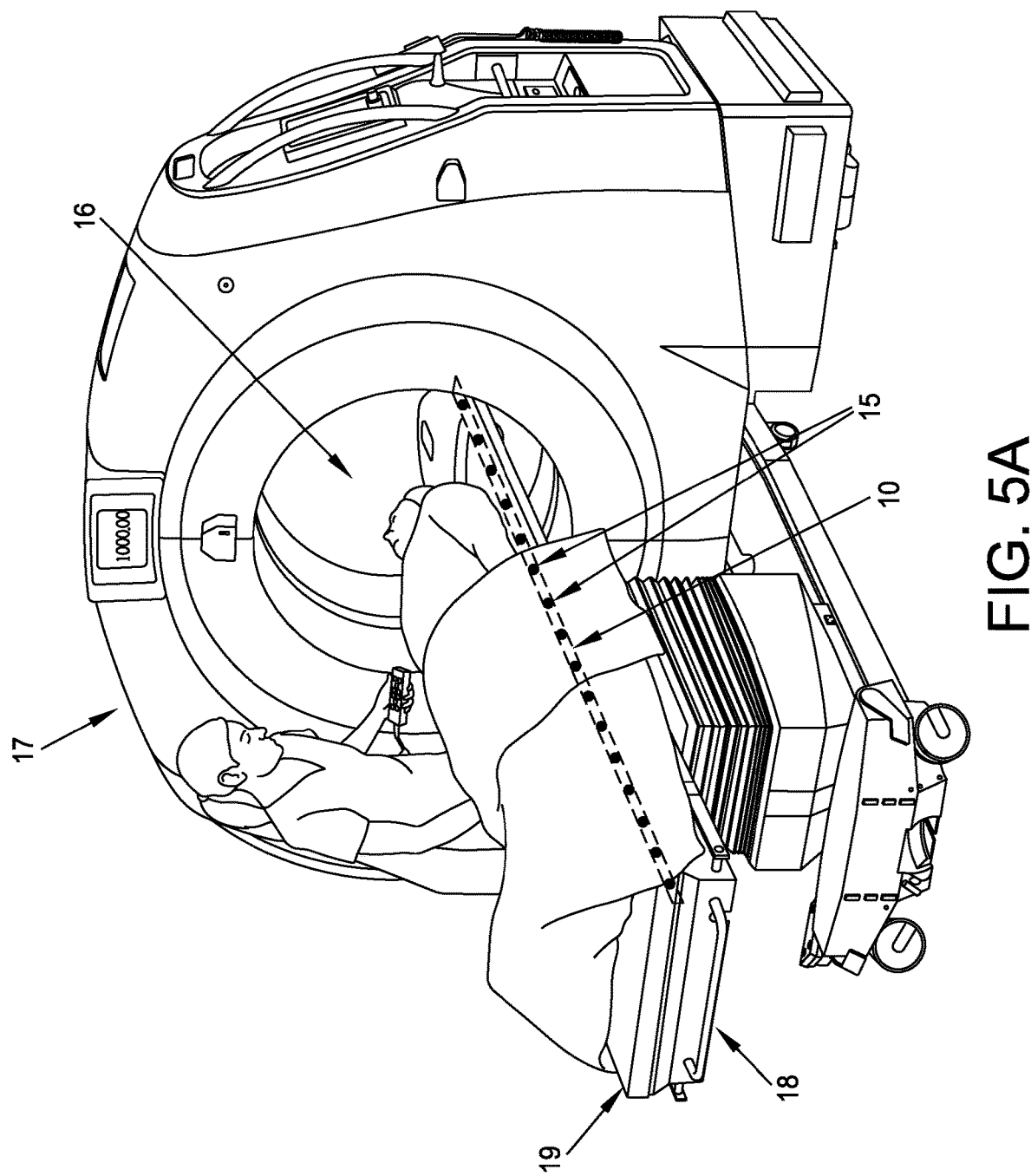
FIG. 5A is a schematic view showing a pre-measured reference (e.g., a ruler with beads) located within the scan field of a scanner so that the pre-measured reference is incorporated into the rendered 3D volume produced by the scan.

The pre-measured reference is, in one preferred form of the invention, a ruler 10 (FIG. 9) with stainless steel beads 15 that are accurately placed along the ruler at a known intervals. The ruler is made long enough to cover any typical scan coverage. The length of the ruler, and the inter-bead intervals, can be defined based on the imaging modality and its purpose. The ruler can be embedded on the patient support or otherwise positioned adjacent to the patient: the only requirement is that the ruler must be located within the imaging space of the modality so that it is incorporated in the scan image. See FIG. 5A, which shows a ruler 10 with stainless steel beads 15 located within the scan field 16 of a scanner 17. By way of example but not limitation, ruler 10 with stainless steel beads 15 may be carried by a patient support 18 which supports the patient within the scan field 16. By way of further example but not limitation, ruler 10 with stainless steel beads 15 may be disposed beneath a cushion 19 which provides the upper surface of patient support 18. Note that while the scanner 17 shown in FIG. 5A is configured to provide "mobile CT imaging" with a mobile CT machine and a fixed patient support, scanner 17 may, alternatively, be configured to provide "fixed CT imaging" with a fixed CT machine and a moving patient support.

Using the 3D volume generated by the imaging modality, in one preferred form of the invention, the auto-correction scheme of the present invention works as follows:

1—Create a rendered 3D volume of the imaged object and the reference ruler;

2—Extract the reference information from the rendered 3D volume, e.g., measure the distances between the beads on the reference ruler in the 3D rendered volume;

3—Compare the extracted information to the true information of the reference ruler, e.g., compare the measured distances between the beads from the 3D rendered volume to the true distances between the beads of the reference ruler;

4—Estimate the extent of the deformation in the scanned volume, based on the above comparison;

5—Correct the rendered 3D volume based on the above estimate;

6—Extract the reference information from the corrected 3D volume, e.g., measure the distances between the beads of the ruler in the corrected 3D volume after the above correction; and 7—Compare the measured reference of the corrected 3D volume to the true reference ruler for validation purposes.

The last two steps are optional, and are only used to validate the auto-correction.

In one preferred form of the invention, the auto-correction scheme of the present invention is implemented by software running on an appropriately-programmed general purpose computer.

The auto-correction scheme of the present invention preferably employs several algorithm tools which may be implemented in software on an appropriately-programmed general purpose computer:

1—Auto-detection: this algorithm tool automatically detects the main components (e.g., ruler 10 and its beads 15) of the reference object which are needed for extracting the correction information. The auto-detection algorithm uses morphology and segmentation. In essence, the auto-detection tool takes the complete rendered 3D volume and extracts the rendered 3D volume of the reference ruler.

2—Auto-matching: this algorithm tool uses sequential matching rules to find (i.e., identify) the components (i.e., the ruler 10 and its beads 15) of the reference phantom (i.e., the rendered 3D volume of the reference ruler). Once the relevant components are identified, the error is estimated by comparing the rendered 3D volume of the reference ruler to actual 3D volume of the reference ruler. In essence, the auto-matching algorithm tool uses sequential matching to correlate the components of the rendered 3D reference to the components of the actual reference, and then estimates the error between the rendered 3D reference and the actual reference.

3—Auto-correction: this algorithm tool then re-samples the imaged volume, based on the outcomes of the auto-matching step, to correct the rendered 3D volume for translational errors of the scanner. In essence, the spacing between the slices of the rendered 3D volume are adjusted so as to provide a corrected rendered 3D volume, and then the corrected rendered 3D volume is re-sampled (i.e., "re-sliced") so as to provide an appropriate set of 2D slice images (e.g., slice images in the DICOM standard) which are reflective of the corrected rendered 3D volume.

These three algorithm tools are contained within the software application which implements the preferred form of the present invention.

The Software Application Which Implements The Preferred Form Of The Invention

The software application which implements the preferred form of the invention reads the DICOM images which are produced by simultaneously scanning the patient anatomy and the pre-measured reference in the same scan field, corrects the rendered 3D volume using the scanned reference, and then outputs a set of corrected images (e.g., in the DICOM standard).

Figure 6:
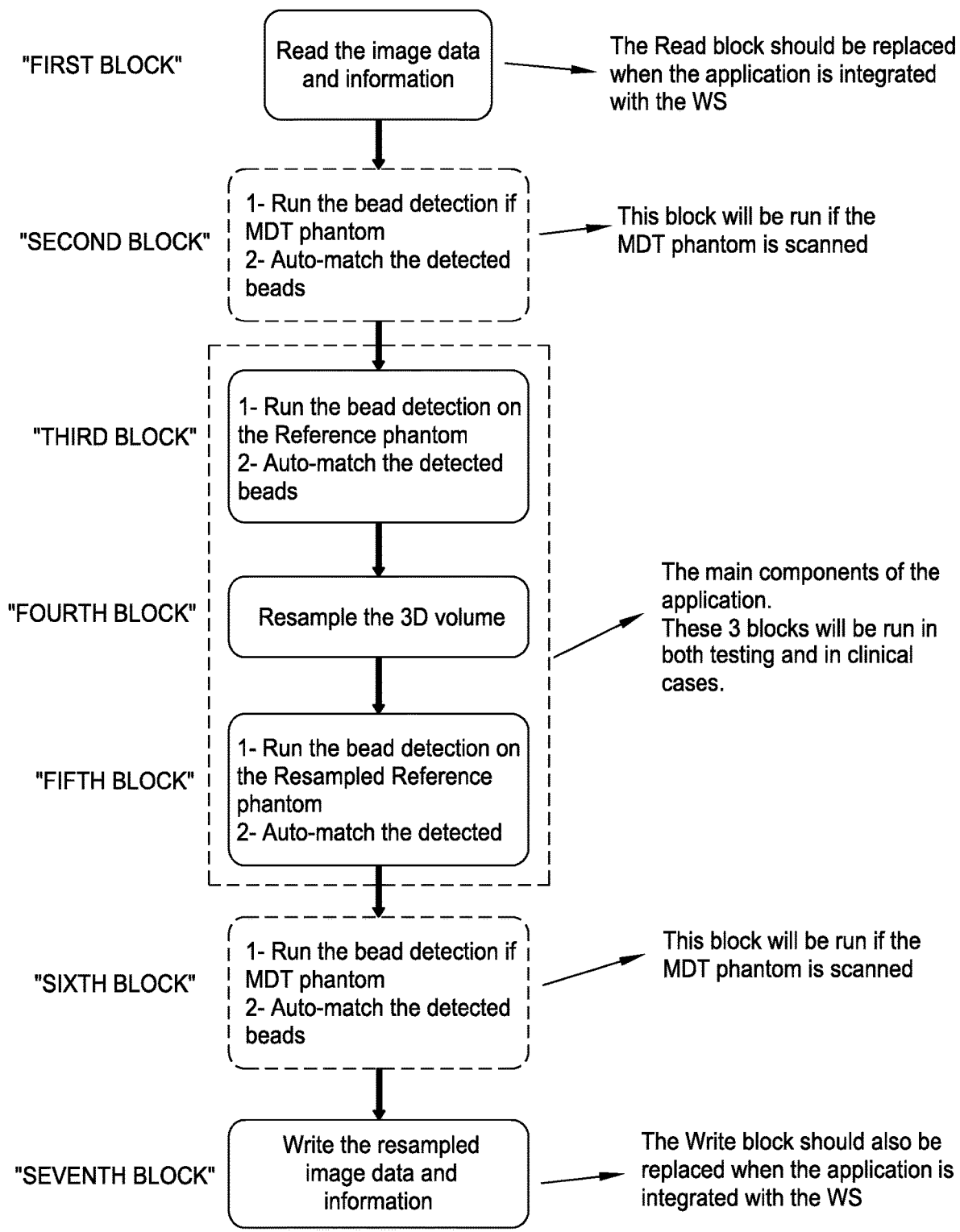
FIG. 6 is a schematic view showing a preferred method for correcting errors introduced into a rendered 3D volume due to the scanner moving at a speed which is different than its intended speed.

The auto-correction scheme of the present invention preferably comprises seven blocks. See FIG. 6. Each block performs a given task. Some of these blocks are optional, based on the purpose of the scan, for example, a validation scan requires the use of a special bead phantom (i.e., the rendered 3D volume of the pre-measured reference). Three essential blocks need to be active in any type of scan. These blocks will use a reference phantom (i.e., the rendered 3D volume of the pre-measured reference) to estimate the error in the scanned volume and apply the correction needed to improve the translational accuracy of the scanner.

The First Block reads the image data or data from a binary file, for example, a DICOM series. The image data includes the reference phantom and the target scan (i.e., the pre-measured reference within the image data). Note that the image data can be from a clinical scan or from a validation scan of the phantom (i.e., the pre-measured reference), either of which can be used to measure the accuracy of the scanned volume.

The Second Block runs the auto-detection algorithm if the system is running a validation scan of a validation phantom (i.e., the pre-measured reference). The validation phantom (i.e., a pre-measured validation phantom which can be the same as the pre-measured reference which is used for a clinical scan) is typically made up of markers set at known distances (e.g., ruler 10 with beads 15, see FIG. 9). This Second Block also runs the auto-matching algorithm to match the scan of the reference markers to the true markers of the validation phantom (i.e., the pre-measured reference).

The Third Block runs the auto-detection and the auto-matching algorithms on the rendered 3D reference phantom (i.e., the rendered 3D volume of the pre-measured reference). In addition to calculating the maximum errors, it also calculates the re-sampling map (i.e., the "correction map") for correcting scanner translation errors in the scanned volume.

The Fourth Block re-samples the scanned volume using the correction map generated earlier. In other words, the Fourth Block adjusts the original rendered 3D volume, using the correction map, to produce a corrected rendered 3D volume, and then this corrected rendered 3D volume is re-sampled (i.e., "re-sliced") so as to produce a corrected set of 2D slice images (e.g., slice images in the DICOM standard) which reflect the corrected rendered 3D volume. The re-sampled volume should be more accurate than the original rendered volume, since it corrects for scanner translational errors. The re-sampled data uses real information about the scan floor to correct the positional accuracy of the scanner.

The Fifth Block is a repeat of the Third Block. However, the corrected volume is used for auto-detecting and auto-matching of the resampled reference phantom (i.e., the pre-measured reference). The block is used to validate the accuracy of the auto-correction performed on the rendered 3D reference phantom (i.e., the pre-measured reference).

The Sixth Block is similar to the Second Block. It runs the auto-detection and auto-matching algorithms on the re-sampled volume. Similar to the Second Block, it will only be applied only if the validation phantom (i.e., the pre-measured validation phantom or pre-measured reference) is used.

The Seventh (and last) Block is used for writing the re-sampled volume to a memory storage unit (e.g., on the scanner, or in a hospital PACS unit, etc.) for later use.

Blocks Three and Four are the only blocks needed for achieving auto-correction of the scanned volume to correct for translational errors of the scanner. The remaining blocks are mainly used for validation and verification purposes. Blocks Three, Four and Five are used in both validation and clinical cases. The First and Seventh (the last) Blocks serve as the interface to the scanner.

The Auto-Detection Algorithm Tool

The auto-detection algorithm is designed to detect the markers of the reference phantom (e.g., the beads 15 of the pre-measured reference ruler 10) or the validation phantom (e.g., a pre-measured reference which may be the same as the clinical reference phantom) in the rendered 3D image. The auto-detection process is a multi-step process:

1—A 2D segmentation step that creates objects in the 2D scan images;

2—The 2D segments are then merged to create 3D objects;

3—The centroid of each detected object is then calculated using the scanner coordinate system;

4—Extract features for each detected marker (e.g., bead 15), i.e., the volume, the average density; and 5—Assign a label for each detected marker (e.g., bead 15).

The objects are created using "the connected component labeling segmentation" method. However, any segmentation method can be used to create the 3D objects. The auto-detection algorithm is parameter-driven so it can be adjusted based on the size and the nature of the reference marker (e.g., bead 15).

The Auto-Matching Algorithm Tool

The detected markers (e.g., beads 15) are automatically matched to a set of reference markers (e.g., the beads 15 of the pre-measured reference ruler 10). The matching is done based on the inner distances between the detected markers and the true markers:

$$M(m_1 \ldots m_n) = \mathrm{argmin}_{all\ permutation}(|\Sigma d_m(i,j) - \Sigma d_t(i,j)|)$$

The matching is done sequentially:
1—A subset of the true markers is selected (typically, a minimum of three markers are selected);
2—The distance measure used for matching is selected—the matching distance can be any combination of the measured features such as distances, directions, volume or any other physical property;
3—The detected markers are then divided into sub-sets of the same size as the subsets of the true markers (the number of subsets can be very large based on the number of detected and true markers—the key is to select small size subset);
4—The first subset is matched using the above equation;
5—Then add one marker to the subset of matched markers;
6—Find the detected marker that can be added to the matched detected markers which minimizes the above equations; and
7—Repeat Steps 6 and 7 until all the true markers are matched to a detected marker.

The Decision Tree

The auto-matching algorithm used a tree-based decision tree with N-best choices. For a set of M markers, the number of possible matches is astronomical, for example, for a set of 13 markers there exists 6,227,020,800 possible matches. For a set of 78 markers, the number of all possible choices is 118 digits long. The decision is based on calculating the matching scores of all possible matches (which is practically impossible). Several methods have been used to make the calculation practical. The N-best choice algorithm, coupled with the sequential search algorithm, will reduce the computation time and allow for a fast decision:
1—The search starts using a subset of markers;
2—Find the highest N scores;
3—Add one marker, compute the next N×M matching scores;
4—Find the highest N scores;
5—Trace back to the root of the decision tree to find the N-best traces;
6—Repeat Steps 3 to 5 until all M markers having been matched; and
7—Select the trace with the best matching score.

Figure 7:
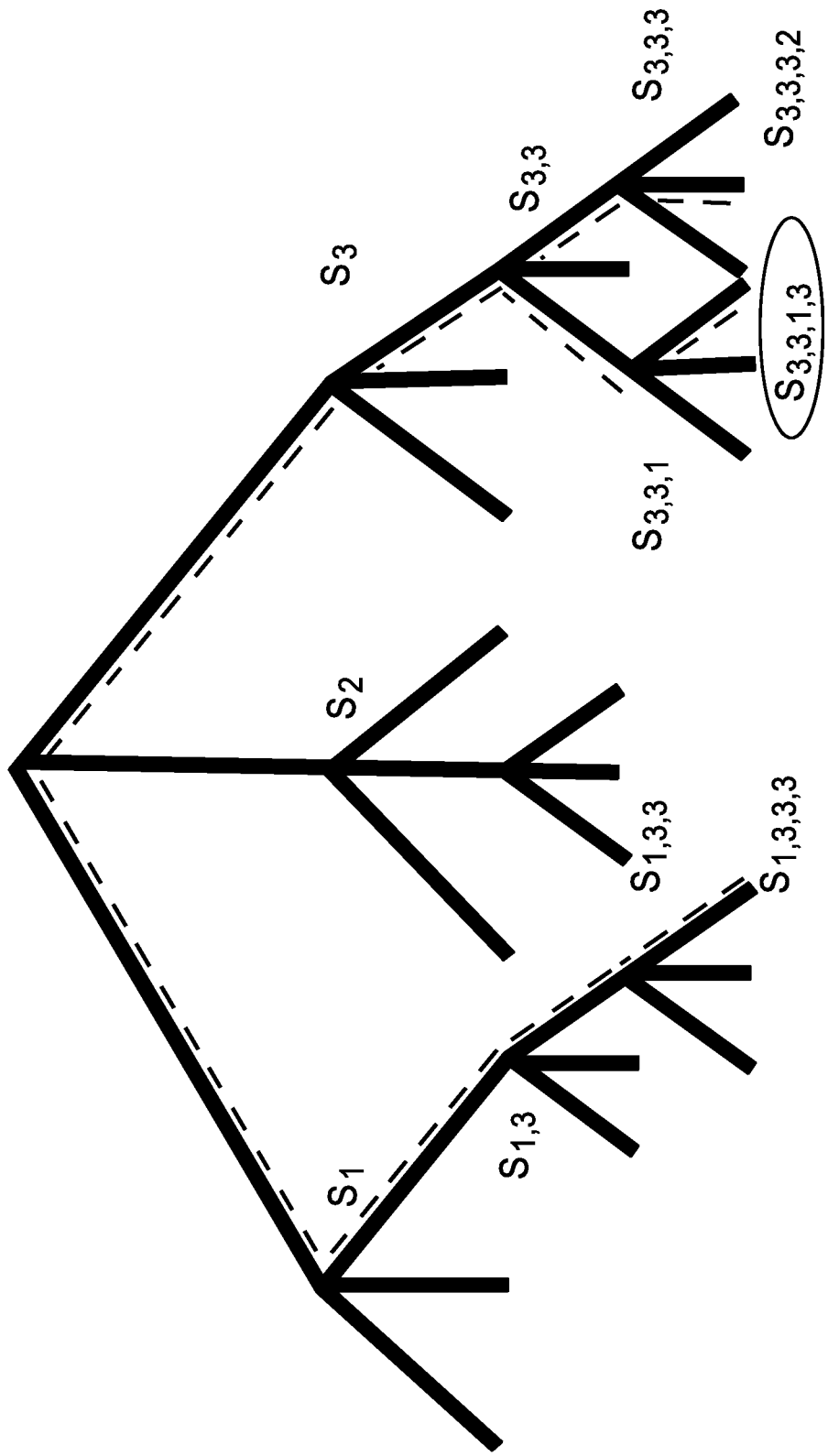
FIG. 7 is a schematic view showing a decision tree which may be used to identify markers in a rendered 3D volume.

FIG. 7 shows the decision tree for the first 3 best choices. The solid line segments represent the 3 best scores at each node or branch of the tree. At the third matching sequence, the middle branch is eliminated from the search. The dashed line traces shows the best three traces with the best three matching scores for all the markers.

The Error Estimation

In general, the imaged (i.e., rendered) 3D volume is made up of a collection of 2D images. The 2D images are assumed to be equi-spaced. However, slight errors in the locations of the 2D images causes the deformation in the scanned volume (these errors in the locations of the 2D images are the result of translational errors of the scanner). For example, if the scanner is moving too slowly, the spacing between the 2D images will be compressed (see FIG. 4); and if the scanner is moving too quickly, the spacing between the 2D images will be expanded (see FIG. 5). The detected markers are used to estimate any deformation or inaccuracy in the scanned volume based on the locations of the detected markers (i.e., the locations of the rendered 3D markers are compared with the locations of the true markers to identify inaccuracies in the scanned volume). The error in the location of each of the 2D slices is calculated using the true and the detected locations of the reference markers. The objective of this step is to estimate the true locations of each scanned slice.

$$E_{location} = f(M_{truelocation}, M_{scannedlocation})$$

The Correction

Based on the estimated locations of the scanned slices, a new 3D volume is created using interpolation of the actual 2D slices. The adjusted 3D volume created by adjusting the spacing of its 2D slices may then be re-sampled (i.e., re-sliced) so as to provide an appropriate set of 2D images (e.g., in the DICOM standard) reflective of the corrected rendered 3D volume. The re-sampled volume should present a more accurate representation of the true volume, since the re-sampled slices of the corrected rendered 3D volume will correct for translational errors of the scanner. The calculated error of the location of each scanned slice is used to re-sample the volume at equi-spaced locations using interpolation of the scanned slices.

$$I(S_{resampled}) = f(E_{location})$$

For instance, for the case where f is a linear interpolation:

$$I(S_{location}) = W_1 M_{pl1} + W_2 M_{pl2}$$

Figure 8:
FIG. 8 is a schematic view which illustrates the auto-correction process for correcting errors introduced into a rendered 3D volume due to the scanner moving at a speed which is different than its intended speed.
Figure 8:
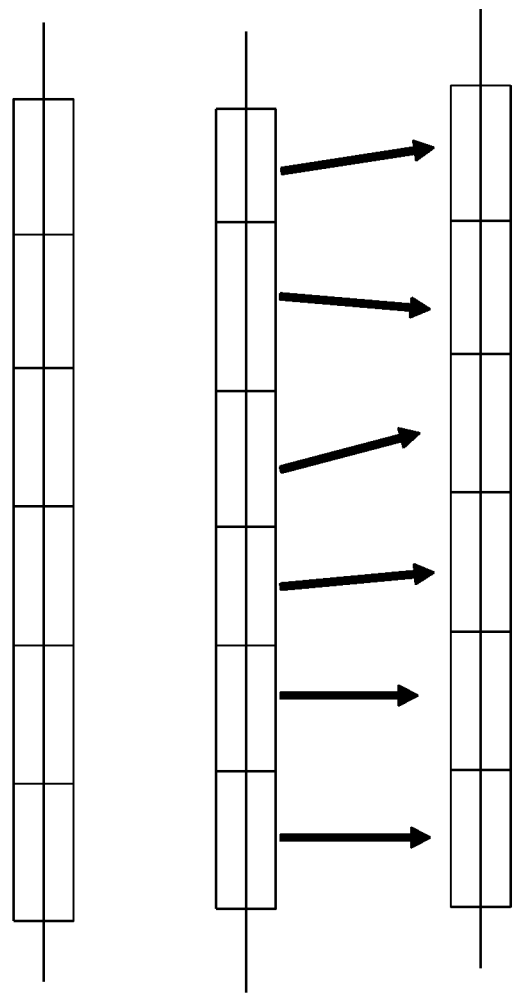

FIG. 8 illustrates the auto-correction process:
1—The top image of FIG. 8 shows the true volume—the scan sections of the true 3D volume are equi-spaced;
2—The middle image of FIG. 8 shows the imaged 3D volume—the centers of the scanned segments are not equi-spaced, however, a comparison of the imaged 3D volume with the true volume can help determine the error of each scanned section; and
3—The bottom image of FIG. 8 shows the corrected imaged volume after interpolation using the comparison results of the error estimation.

The Pre-Measured Reference

Figure 9:
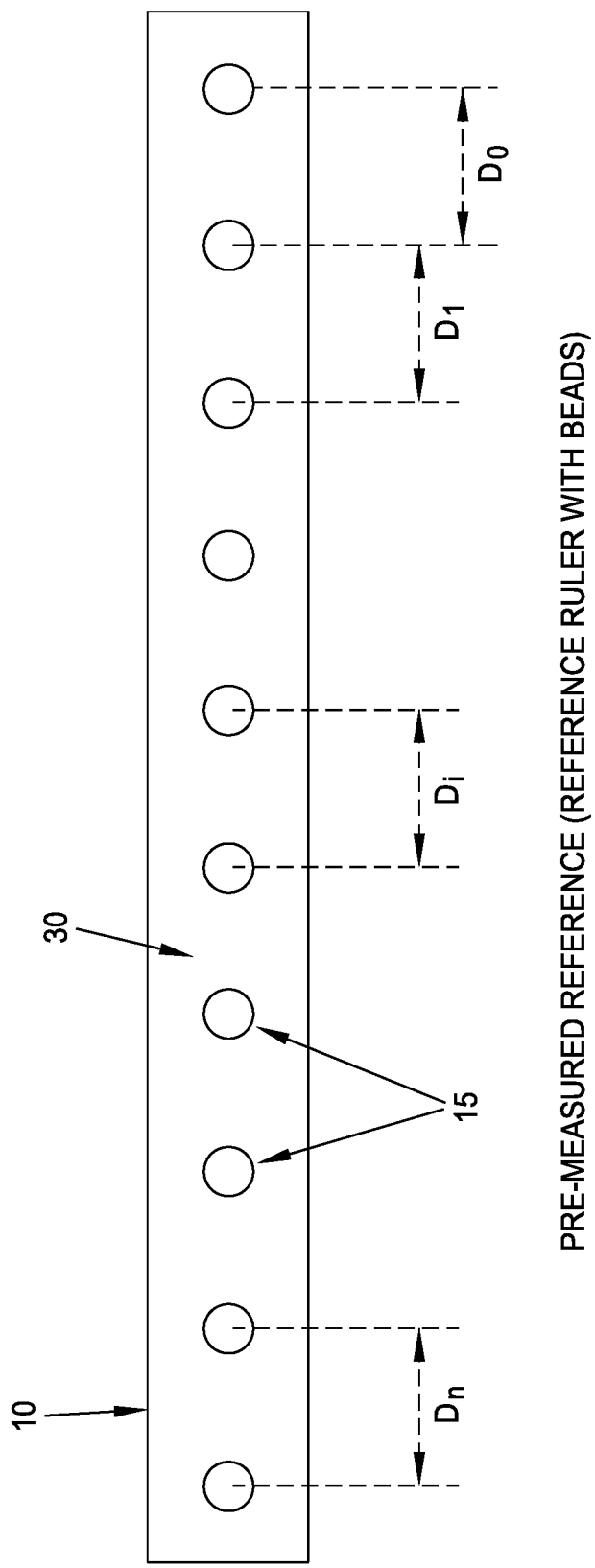
FIG. 9 is a schematic view showing one preferred form of pre-measured reference, wherein the pre-measured reference comprises a radio-transparent ruler with radioopaque beads.

The pre-measured reference can be any configuration that contains a plurality of identifiable objects set with a known spacing. For example, in one preferred form of the invention, the pre-measured reference comprises a ruler 10 with a set of markers in the form of beads 15. The markers can be chosen to minimize their impact on the intended use of the imaging modality. A typical reference is a ruler with high density beads that are placed at given distances or coordinates. FIG. 9 shows a sample ruler 10 comprising a plastic bar 30 with stainless steel beads 15.

Of course, other references can also be used. See FIG. 10.

The pre-measured reference with a plurality of identifiable objects can be placed at any location as long as it is being included in the imaged volume. A typical position would be under the mat of the patient support table, or on the side of a surgical table, or at the bottom of a head holder, etc. These are few of the convenient locations of the reference, but not the only ones.

Modifications Of The Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for correcting inaccuracies in a three-dimensional (3D) rendered volume of an object due to deviations between an actual scanner translation speed and an expected scanner translation speed, the method comprising:
   placing a pre-measured reference adjacent to the object which is being scanned so that the pre-measured reference and the object are in the same scan field;
   scanning the object and the pre-measured reference so that the object and the pre-measured reference are both incorporated in a 3D rendered volume produced through scanning;
   isolating the 3D rendered volume of the pre-measured reference from the 3D rendered volume of the object and the pre-measured reference;
   comparing the 3D rendered volume of the pre-measured reference against the 3D volume of the true pre-measured reference and generating a correction map indicative of how the 3D rendered volume of the pre-measured reference should be adjusted so as to correct inaccuracies in the 3D rendered volume of the pre-measured reference; and
   using the correction map to adjust the 3D rendered volume of the object.

2. A method according to claim 1 wherein the pre-measured reference comprises a plurality of radiopaque markers spaced from one another by a pre-determined distance.

3. A method according to claim 2 wherein the plurality of radiopaque markers are mounted to a radiotranslucent body.

4. A method according to claim 3 wherein the radiopaque markers comprise metal beads and the radiotranslucent body comprises a plastic structure.

5. A method according to claim 1 wherein the object comprises patient anatomy.

6. A method according to claim 1 further comprising the step of re-sampling the adjusted 3D rendered volume of the object so as to provide an appropriate set of two-dimensional (2D) slice images in the DICOM standard.

7. A method according to claim 1 wherein using the correction map to adjust the 3D rendered volume of the object comprises using the correction map to adjust the 3D rendered volume of the object and the pre-measured reference.

8. A method according to claim 7 wherein, after adjusting the 3D rendered volume of the object and the pre-measured reference, the 3D rendered volume of the object is isolated from the 3D rendered volume of the object and the pre-measured reference.

9. A method according to claim 1 wherein using the correction map to adjust the 3D rendered volume of the object comprises isolating the 3D rendered volume of the object from the 3D rendered volume of the object and the pre-measured reference, and then using the correction map to adjust the 3D rendered volume of the object.

10. A method according to claim 1 further comprising the step of using the correction map to determine the actual scanner translation speed.

11. A method according to claim 10 further comprising the step of using the correction map to modify the actual scanner translation speed so that is closer to the expected scanner translation speed.

12. A method according to claim 1 further comprising providing a structure for supporting the object which is being scanned.

13. A method according to claim 12 wherein the object comprises patient anatomy, and the structure comprises a patient support.

14. A method according to claim 13 wherein the patient support comprises a top surface for receiving the patient anatomy, and further wherein the pre-measured reference is carried by the patient support at a location below the top surface.

15. A method according to claim 14 wherein the patient support comprises a scan table covered by a cushion, and further wherein the pre-measured reference is disposed below the cushion.

16. A method for correcting inaccuracies in a three-dimensional (3D) rendered volume of an object due to deviations between an actual scanner translation speed and an expected scanner translation speed, the method comprising:
   creating a 3D rendered volume of the object and a pre-measured reference;
   extracting information regarding the 3D rendered volume of the pre-measured reference from the 3D rendered volume of the object and the pre-measured reference;
   comparing the extracted information regarding the 3D rendered volume of the pre-measured reference to information corresponding to the actual pre-measured reference;
   determining the extent of the deviation of the 3D rendered volume of the pre-measured reference from the information corresponding to the actual pre-measured reference;
   correcting the 3D rendered volume of the object based on the foregoing determination of the extent of the deviation of the 3D rendered volume of the pre-measured reference from the information corresponding to the actual pre-measured reference;
   extracting information regarding the 3D rendered volume of the pre-measured reference from the corrected 3D rendered volume of the object and the pre-measured reference; and
   comparing the extracted information regarding the 3D rendered volume of the pre-measured reference to information corresponding to the actual pre-measured reference.

17. A method according to claim 16 wherein the pre-measured reference comprises a plurality of radiopaque markers spaced from one another by a pre-determined distance.

18. A method according to claim 17 wherein the plurality of radiopaque markers are mounted to a radiotranslucent body.

19. A method according to claim 18 wherein the radiopaque markers comprise metal beads and the radiotranslucent body comprises a plastic structure.

20. A method according to claim 16 wherein the object comprises patient anatomy.

21. A method according to claim 16 further comprising the step of re-sampling the adjusted 3D rendered volume of the object so as to provide an appropriate set of two-dimensional (2D) slice images in the DICOM standard.

22. A method according to claim 16 wherein the step of comparing the extracted information regarding the 3D rendered volume of the pre-measured reference to the information corresponding to the actual pre-measured reference comprises utilizing a decision tree with N-best choices.

23. A method according to claim 16 further comprising the step of using the correction map to determine the actual scanner translation speed.

24. A method according to claim 23 further comprising the step of using the correction map to modify the actual scanner translation speed so that it closer approaches the expected scanner translation speed.

25. A method for correcting inaccuracies in a three-dimensional (3D) rendered volume of an object due to deviations between an actual scanner translation speed and an expected scanner translation speed, the method comprising:

placing a pre-measured reference adjacent to the object which is being scanned so that the pre-measured reference and the object are in the same scan field;

scanning the object and the pre-measured reference so that the object and the pre-measured reference are both incorporated in a 3D rendered volume produced through scanning;

comparing the 3D rendered volume of the pre-measured reference against the 3D volume of the true pre-measured reference and generating a correction map indicative of how the 3D rendered volume of the pre-measured reference should be adjusted so as to correct inaccuracies in the 3D rendered volume of the pre-measured reference; and using the correction map to adjust the 3D rendered volume of the object, wherein using the correction map to adjust the 3D rendered volume of the object comprises isolating the 3D rendered volume of the object from the 3D rendered volume of the object and the pre-measured reference, and then using the correction map to adjust the 3D rendered volume of the object.

\* \* \* \* \*